(12) United States Patent
Schilffarth et al.

(10) Patent No.: US 9,500,644 B2
(45) Date of Patent: Nov. 22, 2016

(54) PARTICLE POPULATIONS AND ASSAYS HAVING VARYING AMOUNTS OF MAGNETIC MATERIAL AND PARTICLE CONCENTRATIONS AMONG DIFFERENT SUBSETS OF PARTICLES AND METHODS FOR PROCESSING ASSAYS HAVING SUCH PARTICLE POPULATIONS

(75) Inventors: Adam Schilffarth, Cedar Park, TX (US); Bruce Bernard, Austin, TX (US); Ben Mize, Austin, TX (US)

(73) Assignee: LUMINEX CORPORATION, Austin, TX (US)

( * ) Notice: Subject to any disclaimer, the term of this patent is extended or adjusted under 35 U.S.C. 154(b) by 1523 days.

(21) Appl. No.: 13/032,316

(22) Filed: Feb. 22, 2011

(65) Prior Publication Data

US 2011/0204874 A1   Aug. 25, 2011

Related U.S. Application Data

(60) Provisional application No. 61/307,076, filed on Feb. 23, 2010.

(51) Int. Cl.
*G01N 33/543* (2006.01)
*B82Y 25/00* (2011.01)
*H01F 1/00* (2006.01)

(52) U.S. Cl.
CPC ......... *G01N 33/54333* (2013.01); *B82Y 25/00* (2013.01); *H01F 1/0054* (2013.01)

(58) Field of Classification Search
CPC .................... G01N 33/54346; G01N 33/587; G01N 33/54353; G01N 2021/6441; B22F 9/24; B22F 1/0018; B22F 2301/255; B22F 2304/054; B22F 2304/056
USPC ......................................... 436/518, 526, 525
See application file for complete search history.

(56) References Cited

U.S. PATENT DOCUMENTS

| | | | |
|---|---|---|---|
| 6,514,295 B1 | 2/2003 | Chandler et al. | 8/607 |
| 6,599,331 B2 | 7/2003 | Chandler et al. | 8/611 |
| 6,632,526 B1 | 10/2003 | Chandler et al. | 428/402 |
| 7,445,844 B2 | 11/2008 | Chandler et al. | 428/403 |
| 2001/0008217 A1 | 7/2001 | Watkins et al. | 210/222 |
| 2001/0046602 A1* | 11/2001 | Chandler et al. | 428/403 |

(Continued)

FOREIGN PATENT DOCUMENTS

WO   WO 2006/079016   7/2006

*Primary Examiner* — Mark Shibuya
*Assistant Examiner* — Pensee Do
(74) *Attorney, Agent, or Firm* — Parker Highlander PLLC

(57) ABSTRACT

Particle populations and assays are provided which have varying amounts of magnetic material and varying particle concentrations among different subsets of particles. In particular, the particle populations and assays include at least two particle sets with distinct sums of particles which are inversely related to the magnetic material concentration comprising each of the particles within the two particle sets, respectively. A method for processing an assay having such particle sets includes routing the assay in proximity to an imaging plane within a static imaging optical analysis system and generating a magnetic field in proximity to the imaging plane. The magnetic field is sufficient to attract and immobilize a ratio of particles from the at least two discrete particle sets that is different from the ratio of particles comprising the at least two discrete particle sets in the assay as the assay is introduced into the static imaging optical analysis system.

16 Claims, 1 Drawing Sheet

(56) References Cited

U.S. PATENT DOCUMENTS

| | | | |
|---|---|---|---|
| 2003/0186465 A1 | 10/2003 | Kraus et al. | 436/5 |
| 2004/0002169 A1 | 1/2004 | Kraus et al. | 435/6 |
| 2006/0127369 A1 | 6/2006 | Christensen et al. | 424/93.7 |
| 2007/0064990 A1 | 3/2007 | Roth | 382/128 |
| 2007/0281311 A1* | 12/2007 | Roth et al. | 435/6 |

* cited by examiner

PARTICLE POPULATIONS AND ASSAYS HAVING VARYING AMOUNTS OF MAGNETIC MATERIAL AND PARTICLE CONCENTRATIONS AMONG DIFFERENT SUBSETS OF PARTICLES AND METHODS FOR PROCESSING ASSAYS HAVING SUCH PARTICLE POPULATIONS

This application claims priority to U.S. Provisional Patent Application Ser. No. 61/307,076 filed Feb. 23, 2010. The entirety of the above-referenced disclosure is incorporated herein by reference.

BACKGROUND OF THE INVENTION

1. Field of the Invention

This invention generally relates to particle populations, assays, and methods for processing assays.

2. Description of the Related Art

The following descriptions and examples are not admitted to be prior art by virtue of their inclusion within this section.

Fluid assays are used for a variety of purposes, including but not limited to biological screenings and environmental assessments. Often, particles are used in fluid assays to aid in the detection of an analyte of interest within a sample. In particular, particles provide a substrate for carrying a reagent configured to react with the analyte of interest within a sample such that the analyte may be detected. In some cases, a multiplexing scheme is employed in assay analysis systems such that multiple analytes may be evaluated in a single analysis process for a single sample. To facilitate a multiplexing scheme, particles are configured into distinguishable groups and each group is used to indicate the presence, absence, and/or amount of a different analyte in an assay. The different particle subsets may be distinguishable, for example, by different fluorescent dyes and/or different concentrations of dyes absorbed into particles and/or bound to the surface of particles. In addition or alternatively, the size of particles among the different subsets may vary. In any case, the number of particles within each particle subset is typically very similar if not the same within an assay. As a consequence, the range of concentrations that can be detected and/or quantified for an assay are generally the same for each analyte of interest.

In some cases, however, it may not be advantageous to analyze all analytes of interest within an assay relative to the same detectable range. On the contrary, in cases in which two or more analytes of interest are present in a sample at significantly different concentrations, it may be advantageous to analyze each analyte of interest relative to a different detectable concentration range such that more comprehensive and accurate analysis results may be obtained with respect to each analyte of interest. However, in order to implement such specificity, the ability to multiplex a sample may be hindered. In particular, a more favorable protocol for the detection and quantification of an analyte of interest in great abundance in a sample includes diluting the sample in order to spread the captured analyte of interest over a greater number of particles and then analyzing each of the dilutions separately to get a reporter response that is within the dynamic range of the detection system. In contrast, a favorable protocol for the detection and quantification of a rare analyte of interest avoids any dilution of a sample in order to maintain the reporter response per particle for the analyte of interest and improve the limit of detection of the analyte of interest. Given the conflicting processing steps of dilution versus no dilution for the different analytes of interest, it is not possible for the two analytes of interests to be analyzed in a multiplex scheme with such protocols.

An alternative approach for facilitating a different detectable range for each analyte of interest within a sample which preserves the use of a multiplex scheme is to employ widely different concentrations of particles among different particle subsets in an assay. In particular, it may be advantageous to have a particle subset with a reactant for an analyte of interest in great abundance in a sample to have a greater concentration of particles within an assay than a particle subset with a reactant for a rare analyte of interest. In this manner, the analyte of interest in great abundance may be spread over a greater number of particles and the reporter response per particle for the rare analyte of interest may be increased. This approach, however, may hinder the ability to obtain accurate results for each analyte of interest when particles are analyzed in batches, such as done in static imaging systems. In particular, the ratio of particles immobilized on an imaging plane for analysis within a static imaging system will generally follow the concentration of particles comprising particle subsets of the assay. Thus, the imaging plane will be populated preferentially with the particle subset/s of relatively higher concentration. In some cases, the particle subset/s of relatively lower concentration may not be present in enough quantity to be statistically significant and, thus, substantive results may not be obtained for the analyte of interest/s associated with the particle subset/s of relatively lower concentration.

Accordingly, it would be desirable to develop methods, systems, particle populations, and assays that allow particles of a particle subset having a relatively lower concentration of particles to be preferentially captured in an imaging chamber over another particle subset having a relatively higher concentration of particles in order to compensate for the difference in particle concentrations dictated by an assay protocol.

SUMMARY OF THE INVENTION

The following description of various embodiments of particle populations, assays, and methods for processing assays is not to be construed in any way as limiting the subject matter of the appended claims.

Embodiments of particle populations, assays, and methods for processing assays include particle populations having a first particle set and a second particle set. In such embodiments, the sum of particles within the first particle set is less than the sum of particles within the second particle set and each particle of the first particle set includes a greater amount of magnetic material than each particle within the second particle set.

Other embodiments of particle populations, assays, and methods for processing assays include particle populations having a plurality of particle sets, wherein at least two particle sets of the plurality of particle sets comprise distinct sums of particles which are inversely related to the magnetic material concentration comprising each of the particles within the at least two particle sets, respectively.

Yet other embodiments of assays and methods for processing assays include particle populations having at least two discrete particle sets distinguishable at least by their distinct concentrations of particles within an assay and the discrete ranges of magnetic material coupled to the particles of the respective particle sets.

Embodiments of methods for processing assays further include introducing an assay including any of the particle populations noted above into a static imaging optical analysis system and routing the assay in proximity to an imaging plane within the static imaging optical analysis system. In addition, the methods include generating a magnetic field in proximity to the imaging plane that is sufficient to attract and immobilize a ratio of particles from at least two discrete particle sets of the assay that is different from the ratio of particles comprising the at least two discrete particle sets in the assay as the assay is introduced into the static imaging optical analysis system. Moreover, the methods include imaging the particles immobilized on the imaging plane and analyzing one or more images produced from said imaging to determine the presence, absence and/or concentrations of one or more analytes of interest within the assay.

BRIEF DESCRIPTION OF THE DRAWINGS

Other objects and advantages of the invention will become apparent upon reading the following detailed description and upon reference to the accompanying drawings in which.

Figure 1:
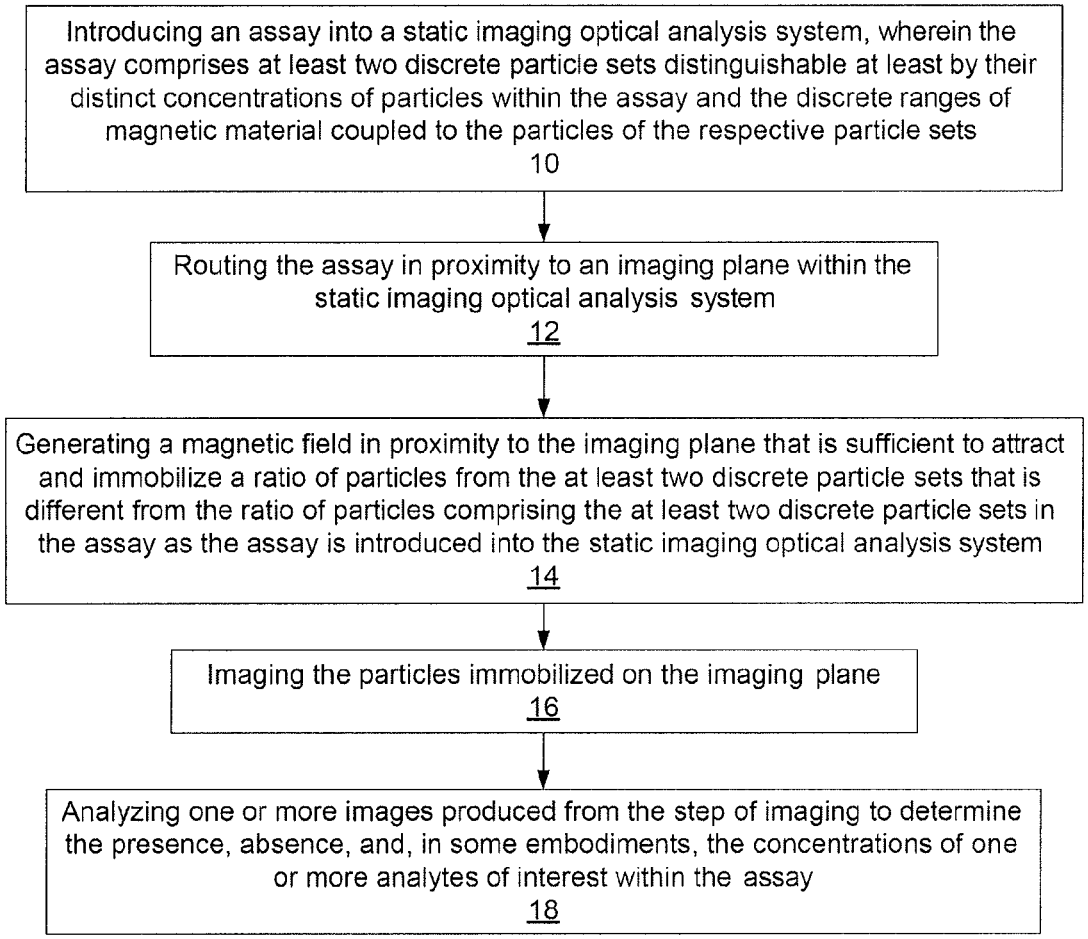
FIG. 1 illustrates a flowchart of a method for processing an assay.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION

Figure 2:
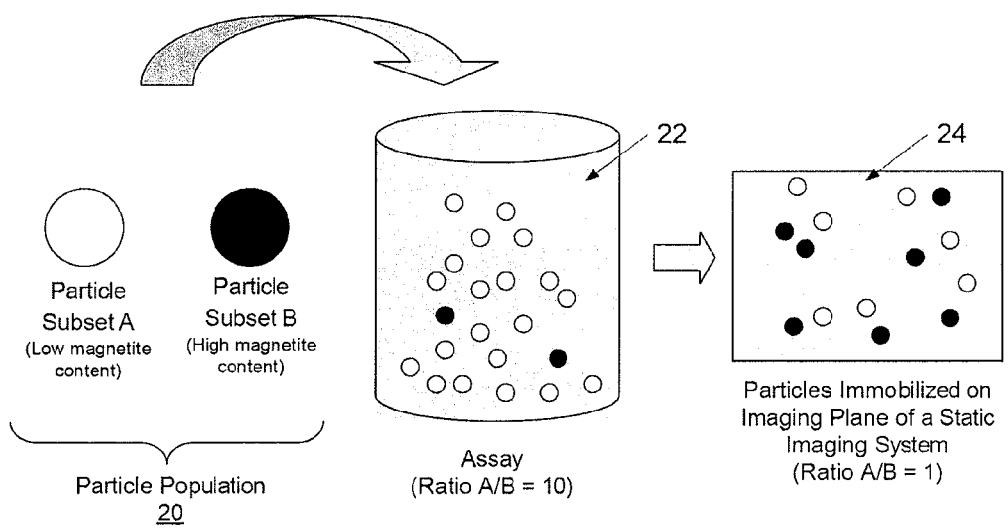
FIG. 2 illustrates a schematic diagram of a particle population, an assay comprising the particle population, and immobilization of some particles of the particle population against an imaging plane of a static imaging system.

Turning to the drawings, exemplary particle populations, assays, and methods for processing an assay are provided. In particular, FIG. 1 illustrates a flowchart of a method for processing an assay. In addition, FIG. 2 illustrates a schematic diagram of a particle population, an assay comprising the particle population, and immobilization of some particles of the particle population against an imaging plane of a static imaging system following the method outlined in FIG. 1. As set forth below, FIGS. 1 and 2 are discussed concurrently to describe aspects of the particle populations, assays, and methods described herein. It is noted, however, that the particle populations, assays, and methods described herein are not necessarily limited to the illustrations of FIGS. 1 and 2. In particular, the particle populations, assays, and methods described herein may include additional or alternative features not shown in FIGS. 1 and 2.

In general, any type of particles may be used for the particle populations, assays, and methods described herein. In some cases, particles serving as vehicles for molecular reactions may be particularly applicable for the particle populations, assays, and methods described herein. Exemplary molecular reaction particles which are used in flow cytometry and static imaging systems include xMAP® and MagPlex™ microspheres, which may be obtained commercially from Luminex Corporation of Austin, Tex. The term "particle" is used herein to generally refer to microparticles, microspheres, polystyrene beads, quantum dots, nanodots, nanoparticles, nanoshells, beads, microbeads, latex particles, latex beads, fluorescent beads, fluorescent particles, colored particles, colored beads, tissue, cells, micro-organisms, organic matter, nonorganic matter, or any other discrete substrates or substances known in the art. Any of such terms may be used interchangeably herein.

In some embodiments, the particles may be encoded such that one subset of particles can be distinguished from another subset. Encoding may be by a variety of techniques. For example, the particles may be fluorescently labeled with fluorescent dyes having different emission spectra and/or different signal intensities. In some embodiments, the size of the particles in a subset may also be used to distinguish one subset from another. Another method of modifying a particle is to incorporate a magnetically responsive substance, such as $Fe_3O_4$, into the structure. In some embodiments, smaller changes in magnetically responsive substances may encode information, and larger changes may be used in conjunction with the particle populations, assays, and methods disclosed herein. Combining fluorescent dyes, particle size, and/or magnetically responsive substances into the particles can further increase the number of different subpopulations of particles that can be created. Another encoding technique that may be used with embodiments of this disclosure is bar-coding. In embodiments, bar coding may be implemented through reflectance modulation, magnetic modulation, and transmission modulation.

As shown in block 10 of FIG. 1, a method of processing an assay includes introducing an assay into a static imaging optical analysis system. The assay includes at least two discrete particle sets distinguishable at least by their distinct concentrations of particles within the assay and the discrete ranges of magnetic material coupled to the particles of the respective particle sets. More specifically, the assay includes a particle population with at least two particle sets having distinct sums of particles which are inversely related to the magnetic material concentration comprising each of the particles within the at least two particle sets, respectively. In some cases, the assay includes a particle population with a first particle set and a second particle set wherein the sum of particles within the first particle set is less than the sum of particles within the second particle set and each particle of the first particle set includes a greater amount of magnetic material than each particle within the second particle set.

Examples of a particle population and an assay which meets the characterization for the assay noted in block 10 of FIG. 1 are illustrated in FIG. 2. In particular, FIG. 2 illustrates particle population 20 having particle subset A with a relatively low magnetite content and particle subset B with a relatively high magnetite content. More specifically, the illustration on the left hand side of FIG. 2 denotes particle population 20 having particle subset A with a plurality of particles each having a relatively low magnetite content coupled and/or incorporated therein and particle subset B with a plurality of particles each having a relatively high magnetite content coupled and/or incorporated therein. As further shown in FIG. 2, particle population 20 is mixed with a biological, chemical, or environmental sample to produce assay 22, the illustration of which shows that particle subset A has a higher concentration of particles than particle subset B in assay 22. Consequently, particle subset A has a higher sum of particles within particle population 20 than particle subset B.

It is noted that the number and ratio of particles shown in each stage of FIG. 2 as well as the number of particle subsets illustrated in FIG. 2 should not be construed to limit the number and/or ratio of particles and/or the number of particle subsets which may be considered for the particle populations, assays, and methods described herein. For instance, an exemplary particle ratio of 10:1 is shown in FIG. 2 for assay 22, but larger and smaller ratios may be considered. In addition, an exemplary particle ratio of 1:1 is shown immobilized against imaging plane 24 in FIG. 2, but larger and smaller ratios may be considered. Furthermore, the number of particles comprising each of particle subsets A and B may be more or less than those shown in assay 22 and/or shown immobilized against imaging plane 24. In fact, fluid assays often include hundreds, thousands, and even millions of particles for biological screenings and environmental assessments and an imaging plane may even be configured to accommodate hundreds or thousands of particles. The low numbers of particles illustrated in assay 22 and shown immobilized against imaging plane 24 in FIG. 2 are merely used to simplify the drawing. The variance in the number of particles illustrated in assay 22 versus the number of particles shown immobilized against imaging plane 24 underscores this assertion in that a larger number of particles from particle subset B are immobilized against imaging plane 24 than are shown to exist in assay 22. Thus, assay 22 must include more particles from particle subset B than shown in FIG. 2. The change in the number of particles shown immobilized against imaging plane 24 for particle subsets A and B relative to those shown in assay 22 is merely used to emphasize the change of particle ratio between the two stages of the method described herein.

Further to such notation, the illustration of a single particle for both particle subsets A and B of particle population 20 on the left hand side of FIG. 2 should not be construed to indicate that each particle subset includes a single particle. On the contrary, particle subsets A and B each include a plurality of particles. The illustration of the single particle for each particle subset A and B on the left hand side of FIG. 2 is merely used to simplify the drawing and distinguish the two particle subsets within particle population 20. Furthermore, although assay 22 is shown to include only two particle subsets, any plurality of particle subsets may be considered for the particle populations, assays, and methods described herein. Moreover, the particles for the particle populations, assays, and methods described herein are not limited to including magnetite as denoted in FIG. 2. Rather, the particles considered for the populations, assays, and methods described herein may include any type of magnetic material. Furthermore, the particle populations, assays, and methods may be applied to any type of assay, specifically any biological, chemical, or environmental assay in which determination of the presence, absence, and/or concentration of one or more analytes of interest is desired. Moreover, although the process denoted in block 10 of FIG. 1 states that the assay is introduced into a static imaging optical analysis system, the particle populations, assays, and methods described herein may be employed by any assay analysis system including but not limited to flow cytometers.

As noted above, the particle populations discussed herein may be described as having at least two particle sets with distinct sums of particles which are inversely related to the magnetic material concentration comprising each of the particles within the particle sets, respectively. In other words, the particle populations described herein may generally have at least two particle populations with distinct sums of particles, wherein the particle set having the greater number of particles has a relatively lower amount of magnetic material coupled to the particles and the particle set having the fewer number of particles has a relatively higher amount of magnetic material coupled to the particles. In some cases, the distinct sums of particles within the particle sets may be inversely proportional to the amount of magnetic material comprising the particles within the particle sets, respectively. In yet further embodiments, the distinct sums of particles within the particle sets may be inversely linear to the amount magnetic material comprising the particles within the particle sets, respectively. As used herein, the phrase "inversely related" refers to a mathematical relationship in which one variable decreases as another variable increases. In contrast, the phrase "inversely proportional" refers to a mathematical relationship in which one variable decreases as another variable increases based on a set function, such as a defined linear function, a defined exponential function, or a defined logarithmic function. And yet, the phrase "inversely linear" refers to a mathematical relationship in which one variable decreases as another variable increases based on a linear function (i.e., the product of the two variables is constant).

In some embodiments, the particle populations, assays, and methods described herein may include at least three particle sets each with distinct sums of particles which are inversely related to the magnetic material concentration comprising each of the particles within the particle sets, respectively. In reference to particle population 20 in FIG. 2, such an embodiment may include a third particle subset with a sum of particles less than the sum of particles within particle set A and/or B. In addition, each particle of the third particle set may include a greater amount of magnetic material than each particle within particle set A and/or B. In some of such cases, the sums of particles within the at least three particle sets and/or the magnetic material concentrations of the particles within the at least three particle sets may be incremented among the at least three particle sets.

In general, the amount of magnetic material comprising each particle of a particle subset may vary slightly. Thus, reference to the magnetic material comprising the particles of a particle subset may be described relative to criterion which is representative of all particles within the particle set in general, such as but not limited to the average amount of magnetic material comprising the particles or a distinct range of magnetic material comprising the particles. For example, in some embodiments, the particles within particle subset A of FIG. 2 may have an average amount of magnetic material which is lower than the average amount of magnetic material comprising the particles of particle subset B. In addition or alternatively, each particle within particle subset A of FIG. 2 may have an amount of magnetic material within a preset range which is distinct and lower than a range of magnetic material comprising each particle of particle subset B. The same such criterion may be used to describe the inverse relationship between the sums of particles within particle sets and the amount of magnetic material comprising the particles of the particle sets described above. For instance, the distinct sums of particles within at least two particle sets may be inversely related, inversely proportional, or inversely linear to the average amounts of magnetic material comprising the particles of the two particle sets, respectively. In addition or alternatively, the distinct sums of particles within at least two particle sets may be inversely related, inversely proportional, or inversely linear to a range of magnetic material comprising each particle of the two particle subsets, respectively.

In any case, the amount magnetic material comprising the particles of a particle population may generally depend on the design specifications of the particle population and the optical analysis system and, thus, may vary widely. An exemplary process for coupling and incorporating magnetic material within particles is described in the U.S. patent application Ser. No. 11/335,139 entitled "Magnetic Microspheres for Use in Fluorescence-Based Applications" by Chandler et al. filed on Jan. 19, 2006, which is incorporated by reference as if set forth fully herein. Other methods, however, may be employed.

Further to the amount of magnetic material comprising each particle of a particle subset varying, the relative amounts of magnetic material comprising particles of different particle subsets may vary among different particle populations, depending on assay protocol. In some embodiments, relatively large differences in amounts of magnetic material among different particle sets, such as differences of an order of magnitude or more, may be particularly suitable for the particle populations, assays, and methods described herein. In particular, it may be advantageous to have each particle of one particle set have at least one order of magnitude more magnetic material than each particle of another particle set. Such large differences in the amount of magnetic material among different particle sets may aid in the preferential capture of particles from a particle subset having a relatively lower particle concentration over another particle set having a relatively higher concentration of particles in an imaging chamber, which as noted above is one of the objectives described herein for overcoming the deficiencies of conventional assay processing. Thus, it may be particularly suitable for the particle populations, assays, and methods described herein to have considerable differences in the amount of magnetic material comprising particles of different particle sets. Smaller differences in amounts of magnetic material among different particle subsets, however, may be used.

Similar to the relative amounts of magnetic materials comprising particles of different particle subsets varying, the relative sums of particles within different particle subsets may vary among different particle populations, depending on assay protocol. In some embodiments, relatively large differences in particle quantity among different particle sets, such as ratios of 1:10 or less (i.e., a sum of particles in one particle set may be one-tenth or less than a sum of particles in the another particle set), may be particularly applicable for the particle populations, assays, and methods described herein. In particular, the larger the difference between quantities of particles among different particle subsets, the greater the need to compensate for the difference in immobilizing particles from the different particle subsets in an imaging chamber. As noted above, it is desirable to have enough particles from each particle subset captured in an imaging chamber such that statistically significant data for each particle subset can be obtained. However, in conventional assay processing, the ability to produce statistically significant data for each particle subset of a particle population becomes more challenging as differences between particles quantities among different particle subsets increase. Consequently, the use of the particle populations, assays, and methods described herein to facilitate the preferential capture of particles from a particle subset having a relatively lower particle concentration over another particle set having a relatively higher concentration of particles may be particularly pertinent for assays having relatively large differences in particle quantities among different particle subsets. Smaller differences in particle sums among different particle subsets, however, may be used.

As noted above, the particle populations, assays, and methods described herein include at least two discrete particle sets distinguishable at least by their distinct sums of particles and the discrete ranges of magnetic material coupled to the particles of the respective particle sets. For multiplexing schemes, the discrete particles sets may be further distinguishable by having different reactants coupled and/or integrated into the particles of the respective particle sets for reacting with different analytes of interest. In other words, the particles of the discrete particle sets may respectively comprise distinct reactants for different analytes of interest. In some cases, different analytes of interest may have substantially different concentration levels in an assay. In such embodiments, it may be advantageous for a particle subset having a reactant for an analyte of interest in great abundance in a sample to have a greater concentration of particles within an assay than a particle subset having a reactant for a rare analyte of interest. In particular, such allocation of varying particle concentrations among different particle sets may allow more comprehensive and accurate analysis results to be obtained with respect to each analyte of interest.

More specifically, varying particle concentrations of different particle sets relative to concentrations of analytes of interest within a sample may allow the analytes of interest to be analyzed relative to different detectable concentration ranges. In particular, an analyte of interest in great abundance in a sample may be captured by a greater number of particles and, thus, will facilitate a reporter response that is within the dynamic range of the detection system. In contrast, a rare analyte of interest in a sample may be captured by fewer particles, effectively increasing the reporter response per particle and improving the limit of detection of the analyte of interest. Given such scenarios, since the sums of particles within at least two discrete particle sets of the particle populations described herein are inversely related to the amounts of magnetic material coupled to and/or incorporated within the particles of the discrete particle sets, the concentrations of different analytes of interest within an assay may in some cases be inversely related to the magnetic material concentration comprising each of the particles within the discrete particle sets.

As noted above, the particle populations, assays, and methods described herein may include any plurality of particle subsets, including but not limited to having tens to hundreds of different particle subsets. In some cases, all of the particle sets of a particle population may be distinguishable at least by their distinct concentrations of particles within the assay and the discrete ranges of magnetic material coupled to and/or incorporated within the particles of the respective particle sets. More specifically, all particle sets of a particle population may have distinct sums of particles which are inversely related to the magnetic material concentration comprising each of the particles within the particle sets, respectively. In some embodiments of such scenarios, the distinct sums of particles of each particle set within a particle population may be inversely proportional and, in further cases, inversely linear to the magnetic material concentration comprising each of the particles within the particle sets, respectively. In addition or alternatively, the sums of particles within the particle sets and/or the magnetic material concentrations of the particles within the particle sets may be incremented among the particle sets.

In other embodiments, however, less than all of the particle sets of a particle population may be distinguishable by their distinct concentrations of particles within the assay and the discrete ranges of magnetic material coupled to the particles of the respective particle sets. As such, the particle populations, assays, and methods described herein may, in some embodiments, include particle subsets that have similar particle quantities and/or similar amounts of magnetic material coupled to and/or incorporated within their particles. Alternatively stated, the particle populations, assays, and methods described herein may, in some embodiments, include at least two particle sets with particle sums which are substantially equal and/or with particles having amounts of magnetic material which are substantially equal. In reference to particle population 20 in FIG. 2, such an embodiment may include a third particle subset, wherein the amount of magnetic material (e.g., the average or range of magnetic material) within the particles of the third particle subset is substantially equal to the amount of magnetic material within the particles of either particle subset A or B. In addition, the third particle subset may include a similar quantity of particles as particle subset A or B. In other embodiments, the particle quantities and amounts of magnetic materials of the third particle subset may be similar to a different particle subset within particle population 20 (i.e., neither of particle subsets A and B).

Turning back to FIG. 1, the method for processing an assay further includes block 12 in which the assay is routed in proximity to an imaging plane within the static imaging optical analysis system. Exemplary static imaging optical analysis systems having a configuration for such a process are described in the U.S. patent application Ser. No. 11/757,841 entitled "Systems and Methods for Performing Measurements of One or More Materials" by Roth et al. filed on Jun. 4, 2007, which is incorporated by reference as if set forth fully herein. Other static imaging optical analysis systems, however, may be used. As noted in block 14 of FIG. 1, the method further includes generating a magnetic field in proximity to the imaging plane that is sufficient to attract and immobilize a ratio of particles from the at least two discrete particle sets that is different from the ratio of particles comprising the at least two discrete particle sets in the assay as the assay is introduced into the static imaging optical analysis system. Such a step is illustrated on the right hand side of FIG. 2 with some particles from both particle subsets A and B immobilized on imaging plane 24 and, more specifically, a lower ratio of particles from particle subsets A and B immobilized on imaging plane 24 than in assay 22 in the middle portion of FIG. 2.

As noted above, the particle populations, assays, and methods described herein are configured such that particles from a particle subset having a relatively lower particle concentration are preferentially captured against an imaging plane over particles of another particle set having a relatively higher concentration of particles. In general, the number of particles immobilized on the imaging plane from each of the discrete particle sets is preferably sufficient such that the data collected for each of the discrete particle sets during the subsequent step of analyzing (i.e., block 18 of FIG. 1) is statistically significant. Such a number is arbitrary depending on for example the assay protocol and the number of particles which may be captured on a given imaging plane. It is noted that the reduction of the particle ratio of 10:1 in assay 22 to the particle ratio of 1:1 immobilized on imaging plane 24 in FIG. 2 is merely exemplary. In particular, the particle populations, assays, and methods described herein may include any ratio of particles prior to immobilization on an imaging plane and, therefore, the particle populations, assays, and methods described herein are not limited to a 10:1 ratio of particles among particle subsets. Furthermore, the particle populations, assays, and methods described herein may be configured to immobilize any ratio of particles on an imaging plane and, therefore, the particle populations, assays, and methods described herein are not limited to immobilizing a 1:1 ratio of particles against an imaging plane. Moreover, the particle populations, assays, and methods described herein are not limited to immobilizing a ratio of particles by a set amount relative to a ratio of particles within an assay. Therefore, the particle populations, assays, and methods described herein are not limited to immobilizing a ratio of particles ten times greater than a ratio of particles in an assay as illustrated in FIG. 2. Smaller or larger amounts may be considered.

In general, the magnetic field referred to in block 14 of FIG. 1 may be generated by any feasible manner known in the art. In some exemplary embodiments, the static imaging optical analysis system may include a magnet on an actuating arm and may further include configurations for moving the magnet in the vicinity of the imaging plane via the actuating arm. In this manner, particles may be drawn to the imaging plane when the magnet is brought in proximity to the imaging plane. In addition, particles immobilized on the imaging plane may be released from the imaging plane when the magnet is drawn away.

Upon or after immobilizing particles upon the imaging plane, the immobilized particles may be imaged as noted in block 16 of FIG. 1. The imaging process may depend on the configuration of the static imaging optical analysis system and, thus, may vary among systems. In general, however, the imaging components of a static imaging optical analysis system may generally include one or more illumination sources and one or more detectors for collecting light generated by the illuminated particles (e.g., fluorescence, light scatter, etc.). The one or more detectors may include photomultiplier tubes (PMT), avalanche photodiodes (APD), one- or two dimensional charge coupled devices (CCD), or another suitable array detector for fluorescence detection. In some embodiments, the static imaging optical analysis system may include additional components, such as filters and/or lens.

In some cases, the static imaging optical analysis system may be configured to image all particles immobilized on an imaging plane at once. In other embodiments, however, the static imaging optical analysis system may be configured to scan the imaging plane during the imaging process and, thus, may be configured to image different regions of the imaging plane (and, thus, different groupings of particles immobilized on the imaging plane) serially. In either case, the static imaging optical analysis system may, in some embodiments, be configured to image the immobilized particles at different wavelengths such that different data may be generated and analyzed regarding the particles. In particular, images generated at different wavelengths may offer different information regarding particles (such as a particle's classification to a particle subset and the concentration of an analyte of interest associated with the particle). Exemplary static imaging optical analysis systems having such configurations are described in the U.S. patent application Ser. No. 11/757,841 entitled "Systems and Methods for Performing Measurements of One or More Materials" by Roth et al. filed on Jun. 4, 2007, which is incorporated by reference as if set forth fully herein. Other static imaging optical analysis systems and configurations, however, may be used.

As noted in block 18 of FIG. 1, the one or more images produced from the imaging process noted in block 16 may be analyzed to determine the presence, absence, and, in some embodiments, the concentrations of one or more analytes of interest within the assay. In some cases, the analysis process denoted in block 18 may include determining the identity or classification of each particle within the image/s. In this manner, measurement values associated with the different particle subsets can be distinguished and, in some cases, respectively attributed to analytes of interest associated with the different particle subsets. As noted above, imaging particles at different wavelengths may generally offer different data to be generated regarding the particles, some of which may be correlated to a particle's classification to a particle subset and the concentration of an analyte of interest associated with the particle.

It will be appreciated to those skilled in the art having the benefit of this disclosure that this invention is believed to provide particle populations and assays which have varying amounts of magnetic material and particle concentrations among different subsets of particles. In addition, a method for processing an assay having such particle subsets is provided. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method, comprising:
   introducing an assay into a static imaging optical analysis system, wherein the assay comprises (i) one or more analytes of interest, and (ii) at least two discrete particle sets distinguishable at least by their distinct concentrations of particles within the assay and the discrete ranges of magnetic material coupled to the particles of the respective particle sets;
   routing the assay in proximity to an, imaging plane within the static imaging optical analysis system;
   generating a magnetic field in proximity to the imaging plane that is sufficient to attract and immobilize a ratio of particles from the at least two discrete particle sets that is different from the ratio of particles comprising the at least two discrete particle sets in the assay as the assay is introduced into the static imaging optical analysis system;
   imaging the particles immobilized on the imaging plane; and
   analyzing one or more images produced from the step of imaging to determine the presence, absence and/or concentrations of the one or more analytes of interest within the assay.

2. The method of claim 1, wherein the distinct concentrations of particles of the at least two discrete particle sets are inversely related to the amount of magnetic material coupled to the particles of the at least two discrete particle sets.

3. The method of claim 1, wherein the number of immobilized particles on the imaging plane from each of the two discrete particle sets is sufficient such that the data collected for each of the two discrete particle sets during the step of analyzing is statistically significant.

4. The method of claim 1, wherein the at least two discrete particle sets are further distinguishable by different reactants coupled to the particles of the respective particle sets, wherein the different reactants are reactive with different analytes of interest within the assay, and wherein concentrations of the different analytes of interest within the assay are inversely related to the amount of magnetic material coupled to the particles of the at least two discrete particle sets.

5. The method of claim 1, where in the particles in the particle sets are encoded with fluorescent labels such that one set of particles can be distinguished from another set of particles based on different emission spectra and/or different emission intensities.

6. The method of claim 5, wherein each of the particles in the particle sets are are encoded with two different fluorescent labels.

7. A method for imaging a population of magnetic particles comprising:
   introducing a population of magnetic particles into a static imaging optical analysis system, wherein the population of magnetic particles comprises a first particle set and a second particle set, wherein the average amount of magnetic material in particles of the first particle set is greater than the average amount of magnetic material in particles of the second particle set, and the sum of particles in the first particle set is less than the sum of particles in the second particle set;
   generating a magnetic field in proximity to an imaging plane in the static imaging optical analysis system that is sufficient to attract and immobilize particles from the first and second particle sets such that the ratio of particles of the first particle set to particles of the second particle set immobilized on the imaging plane is greater than the ratio of particles of the first particle set to particles of the second particle set in the population of magnetic particles introduced into the static imaging optical analysis system; and
   imaging the particles immobilized on the imaging plane.

8. The method of claim 7, wherein the sum of particles in the first particle set is less than one-tenth the sum of particles in the second particle set when the population of magnetic particles is introduced into the static imaging optical analysis system.

9. The method of claim 7, wherein the ratio of particles of the first particle set to particles of the second particle set immobilized on the imaging plane is about 1:1.

10. The method of claim 7, wherein each particle of the first particle set contains at least one order of magnitude more magnetic material than each particle of the second particle set.

11. The method of claim 7, where in the particles in the first and second particle sets are encoded with fluorescent labels such that the first set of particles can be distinguished from the second set of particles based on different emission spectra and/or different emission intensities.

12. A method for multiplex detection of analytes comprising:
   obtaining a population of magnetic particles comprising a first particle set and a second particle set, wherein the average amount of magnetic material in particles of the first particle set is greater than the average amount of magnetic material in particles of the second particle set, the sum of particles in the first particle set is less than the sum of particles in the second particle set, and the particles of the first particle set comprise a first reagent configured to react with a first reagent of interest and the particles of the second particle set comprise a second reagent configured to react with a second reagent of interest;

combining the population of magnetic particles with a sample comprising the first and second reagents under conditions suitable for the first and second reagents to react with the first and second analytes, respectively, wherein the amount of the first analyte in the sample is lower than the amount of the second analyte in the sample;

introducing the population of magnetic particles into a static imaging optical analysis system;

generating a magnetic field in proximity to an imaging plane in the static imaging optical analysis system that is sufficient to attract and immobilize particles from the first and second particle sets such that the ratio of particles of the first particle set to particles of the second particle set immobilized on the imaging plane is greater than the ratio of particles of the first particle set to particles of the second particle set in the population of magnetic particles introduced into the static imaging optical analysis system;

imaging the particles immobilized on the imaging plane; and detecting the presence or absence of the first and second analytes on the particles.

13. The method of claim 12, wherein the ratio of particles of the first particle set to particles of the second particle set is less than 1:10 when the population of magnetic particles is introduced into the static imaging optical analysis system.

14. The method of claim 12, wherein the ratio of particles of the first particle set to particles of the second particle set immobilized on the imaging plane is about 1:1.

15. The method of claim 12, wherein each particle of the first particle set contains at least one order of magnitude more magnetic material than each particle of the second particle set.

16. The method of claim 12, where in the particles in the first and second particle sets are encoded with fluorescent labels such that the first set of particles can be distinguished from the second set of particles based on different emission spectra and/or different emission intensities.

* * * * *

UNITED STATES PATENT AND TRADEMARK OFFICE
CERTIFICATE OF CORRECTION

PATENT NO. : 9,500,644 B2
APPLICATION NO. : 13/032316
DATED : November 22, 2016
INVENTOR(S) : Adam Schilffarth et al.

It is certified that error appears in the above-identified patent and that said Letters Patent is hereby corrected as shown below:

In the Claims

In Claim 1, Column 11, Line 39, delete "an, imaging" and replace with --an imaging-- therefor.

In Claim 5, Column 12, Line 6, delete "where in" and replace with --wherein-- therefor.

In Claim 6, Column 12, Line 12, delete "sets are are encoded" and replace with --sets are encoded-- therefor.

In Claim 11, Column 12, Line 49, delete "where in" and replace with --wherein-- therefor.

In Claim 16, Column 14, Line 15, delete "where in" and replace with --wherein-- therefor.

Signed and Sealed this
First Day of May, 2018

Andrei Iancu
*Director of the United States Patent and Trademark Office*